US00PP27992P3

(12) United States Plant Patent
Klemm et al.

(10) Patent No.: US PP27,992 P3
(45) Date of Patent: May 9, 2017

(54) ***FUCHSIA* PLANT NAMED 'KLEFU14843'**

(50) Latin Name: ***Fuchsia* sp.**
Varietal Denomination: KLEFU14843

(71) Applicant: Klemm+Sohn GmbH & Co. KG, Stuttgart (DE)

(72) Inventors: Nils Klemm, Stuttgart (DE); Andrea Dohm, Pforzheim (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 161 days.

(21) Appl. No.: 14/545,972

(22) Filed: Jul. 13, 2015

(65) Prior Publication Data

US 2017/0020047 P1 Jan. 19, 2017

(51) Int. Cl.
*A01H 5/02* (2006.01)

(52) U.S. Cl.
USPC ..... Plt./300

(58) Field of Classification Search
USPC ..... Plt./263.1, 300
See application file for complete search history.

*Primary Examiner* — Susan McCormick Ewoldt
*Assistant Examiner* — Karen Redden
(74) *Attorney, Agent, or Firm* — Barbara Campbell; James M. Weatherly; Cochran Freund & Young, LLC

(57) ABSTRACT

A new *fuchsia* plant particularly distinguished by flowers having white petals and red-purple sepals, a compact, mounded, upright plant habit, and a freely-branching growth habit, is disclosed.

1 Drawing Sheet

Genus and species: *Fuchsia* sp.
Variety denomination: 'KLEFU14843'.

BACKGROUND OF THE NEW PLANT

The present invention comprises a new and distinct variety of *fuchsia,* botanically known as *Fuchsia* sp. and hereinafter referred to by the variety name 'KLEFU14843'. 'KLEFU14843' originated from a controlled-cross in October 2011 between the proprietary female *fuchsia* variety '2012.15' (unpatented) and the proprietary male *fuchsia* variety '2012.7' (unpatented).

In May 2012, the two *fuchsia* parental lines '2012.15' and '2012.7' were crossed in Stuttgart, Germany and seeds were obtained. The seeds were sown and plants were grown for evaluation. A plant line was selected in March 2013 and subsequently named 'KLEFU14843'. In March 2013, 'KLEFU14843' was first vegetatively propagated by vegetative cuttings in Stuttgart, Germany. 'KLEFU14843' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Flowers having white petals and red-purple sepals;
2. A compact, mounded, upright plant habit; and
3. A freely-branching growth habit.

DESCRIPTION OF THE PHOTOGRAPH

This new *fuchsia* plant is illustrated by the accompanying photograph which shows an overall view of the plant. The photograph is of an approximately 3-month-old plant grown in Stuttgart, Germany under greenhouse conditions in May 2014.

The colors shown are as true as can be reasonably obtained by conventional photographic procedures.

DESCRIPTION OF THE NEW VARIETY

The following detailed descriptions set forth the distinctive characteristics of 'KLEFU14843'. The data which define these characteristics were collected from asexual reproductions carried out in Latina, Italy. Data was collected on 2.5 to 3 month-old plants in Latina, Italy grown in a greenhouse in June 2015. Color references are to The R.H.S. Colour Chart of The Royal Horticultural Society of London (R.H.S.), 5$^{th}$ edition (2007).

Classification:
- *Family.*—Onagraceae.
- *Botanical.*—*Fuchsia* sp.
- *Designation.*—'KLEFU14843'.

Parentage:
- *Female parent.*—The proprietary female *fuchsia* variety '2012.15' (unpatented).
- *Male parent.*—The proprietary male *fuchsia* variety '2012.7' (unpatented).

Propagation:
- *Type.*—Vegetative cuttings.
- *Time to initiate roots, summer.*—About 1 to 2 weeks at 20 ° C. to 25° C.
- *Time to initiate roots, winter.*—About 2 weeks at temperatures of 18° C. to 22° C.
- *Time to produce a rooted young plant, summer.*—3 to 4 weeks at temperatures of 20° C. to 25° C.
- *Time to produce a rooted young plant, winter.*—4 weeks at temperatures of 18° C. to 22° C.

*Root description.*—Fine, fibrous, yellowish-white in color.

*Rooting habit.*—Freely branching; medium density.

Plant:

*Plant habit/form.*—Compact, mounded, upright plant habit.

*Growth habit.*—Freely-branching habit with lateral branches developing potentially at every node; bushy plant habit; vigorous growth habit.

*Plant height.*—20.0 cm to 22.0 cm.

*Plant diameter.*—28.0 cm to 30.0 cm.

Lateral branches:

*Length.*—Approximately 15.0 cm to 18.0 cm.

*Diameter.*—Approximately 2.0 mm.

*Internode length.*—Approximately 2.8 cm.

*Strength.*—Strong, flexible.

*Aspect.*—Initially upright to semi-upright.

*Texture.*—Pubescent.

*Color.*—Close to RHS 146B.

Leaves:

*Arrangement.*—Opposite, simple.

*Length.*—4.7 cm on average.

*Width.*—1.5 cm on average.

*Shape.*—Ovate.

*Apex.*—Broadly acute.

*Base.*—Obtuse and rounded.

*Margin.*—Shallowly serrate.

*Texture* (*both upper and lower surfaces*).—Glabrous.

*Venation pattern.*—Pinnate; arcuate.

*Venation color.*—Upper surface: Close to RHS 146B. Lower surface: Close to RHS 147C.

*Color.*—Developing leaves: Upper surface: RHS 137A. Lower surface: RHS 147B. Fully expanded leaves: Upper surface: RHS N137A. Lower surface: RHS 147B.

Petiole:

*Length.*—Approximately 1.5 cm.

*Diameter.*—Approximately 1.5 mm.

*Texture.*—Upper surface: Smooth, glabrous, concave. Lower surface: Smooth, glabrous, convex.

*Color.*—Upper surface: RHS 146B. Lower surface: RHS 146C.

Flower:

*Flower arrangement and habit.*—Single axillary flowers; flowers pendulous; freely flowering habit with potentially two flowers per leaf axil.

*Total number of flowers per plant.*—Over 40 fully open flowers and 80 buds on a mature plant when at flowering stage.

*Fragrance.*—None detected.

*Natural flowering season.*—Long flowering period; in Europe, plants flower from early spring to autumn; flowering continuous during this period.

*Flower longevity.*—Flowers last about four to six days on the plant.

*Flower diameter.*—0.9 cm (petals), 4.4 cm (sepals).

*Flower height* (*depth*).—Approximately 3.5 cm (base of sepals to stigma tip).

*Flower buds.*—Shape: Elliptic. Length: Approximately 2.5 cm. Diameter: Approximately 0.9 cm. Color: RHS 51A.

Petals:

*Arrangement.*—Typically four in a single whorl.

*Length.*—Approximately 1.5 cm.

*Width.*—Approximately 1.1 cm.

*Shape.*—Obovate.

*Apex.*—Obtuse.

*Base.*—Cuneate.

*Margin.*—Entire.

*Texture* (*both upper and lower surfaces*).—Smooth, glabrous, satiny.

*Color.*—Upper (outside) surface: When opening: RHS 155B. Fully open: RHS 155B. Lower (inside) surface: When opening: RHS 155B. Fully open: RHS 155B.

Sepals:

*Arrangement.*—Calyx star-shaped with four sepals fused at the base.

*Length.*—2.6 cm.

*Width.*—0.7 cm.

*Shape.*—Elliptic.

*Apex.*—Slightly cuspidate.

*Base.*—Attenuate, fused.

*Margin.*—Entire.

*Texture* (*both upper and lower surfaces*).—Smooth, glabrous, and satiny.

*Color.*—Upper (outside) surface: When opening: RHS 58B. Fully opened: RHS 58B. Lower (inside) surface: When opening: RHS 58B. Fully opened: RHS 58C.

Peduncles:

*Length.*—2.6 cm on average.

*Diameter.*—0.09 cm.

*Angle.*—Arching.

*Strength.*—Moderately strong.

*Texture.*—Sparsely pubescent.

*Color.*—RHS 146B.

Reproductive organs:

*Stamens.*—Quantity per flower: 8. Anther shape: Ellipsoidal. Anther size: About 2.2 mm by 1.3 mm. Anther color: RHS 158B with RHS N57B (Red-Purple) shading. Pollen amount: Scarce. Pollen color: Close to RHS 155A.

*Pistils.*—Quantity: 1 per flower. Pistil length: 4.5 cm on average. Style color: Towards the base, close to RHS 155A; towards the apex, close to RHS 54A. Stigma shape: Clavate. Stigma color: RHS 49B. Ovary color: RHS 144A.

Fruit and seed set: None observed.

Disease and pest/insect resistance: None observed.

COMPARISON WITH PARENTAL LINES AND KNOWN VARIETY

'KLEFU14843' is distinguished from its parents as described in Table 1:

TABLE 1

| Comparison with Parental Lines | | | |
|---|---|---|---|
| Trait | 'KLEFU14843' | Female parent '2012.15' | Male parent '2012.7' |
| Plant habit | Mounded | Semi-mounded | Semi-mounded |

'KLEFU14843' can be compared to the commercial variety WINDCHIMES 'Red White' (patent status unknown). Differences between the two varieties are described in Table 2:

TABLE 2

| Comparison with Similar Variety | | |
|---|---|---|
| Trait | 'KLEFU14843' | Commercial line WINDCHIMES 'Red White' |
| Sepal color | Light red | Dark red |

We claim:

1. A new and distinct variety of *fuchsia* plant named 'KLEFU14843' as illustrated and described herein.

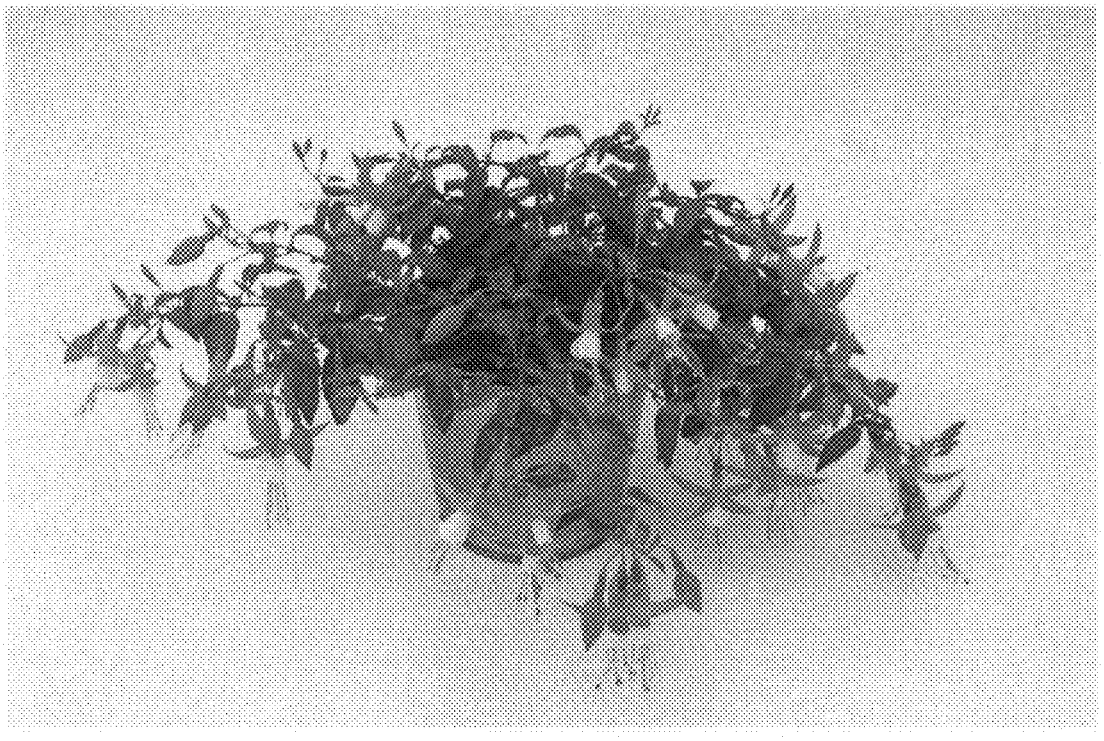

* * * * *